United States Patent [19]
Astle

[11] Patent Number: 5,260,028
[45] Date of Patent: Nov. 9, 1993

[54] METHOD AND APPARATUS FOR EFFECTING SOLID PHASE EXTRACTION

[76] Inventor: Thomas W. Astle, 607 Harborview Rd., Orange, Conn. 06477

[21] Appl. No.: 891,865

[22] Filed: Jun. 1, 1992

Related U.S. Application Data

[62] Division of Ser. No. 158,902, Feb. 22, 1988, abandoned.

[51] Int. Cl.⁵ .................... G01N 30/04; G01N 30/14; G01N 30/24
[52] U.S. Cl. .......................... 422/81; 422/65; 422/67; 422/101; 210/635; 210/641
[58] Field of Search ................. 422/65, 67, 68.1, 81, 422/99, 101; 210/635, 638, 641

[56] References Cited

U.S. PATENT DOCUMENTS 3,578,412  1/1968  Martin ................................. 23/259
3,883,305  5/1975  Hoskins et al. ................... 23/253 R

OTHER PUBLICATIONS

Dimson, P. et al. "Automating Solid Phase Extraction for HPLC Sample Prep." American Laboratory, Oct. 1986 pp. 82-94.

Primary Examiner—James C. Housel
Assistant Examiner—Daniel Redding
Attorney, Agent, or Firm—John H. Crozier

[57] ABSTRACT

A method and apparatus for practicing solid phase extraction of samples for analysis where the method comprises the steps of providing a cassette having a plurality of tubes, each containing an absorbent substrate and having an upper and a lower opening; applying a preconditioning liquid reagent to each tube of the cassette through the upper opening to render the substrate therein hydrophilic and drawing the liquid through the substrate until the liquid is at a predetermined height about the substrate; applying a liquid sample to be analyzed to each of the tubes of the cassette and drawing the sample through the substrate until the liquid is at a predetermined height in the tube with respect to the substrate; applying an eluate to each tube of the cassette to remove an eluent therefrom; and collecting the eluents from the cassette tubes. The apparatus automates this process and provides accurate and rapid separation of compounds in the sample. The process provides the further step of washing the substrate before addition of the eluate, if necessary, and optional drying of the substrate as well as addition of a second eluate to separate a second eluent if desired.

18 Claims, 12 Drawing Sheets

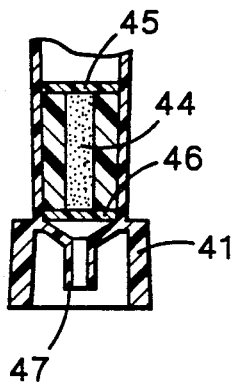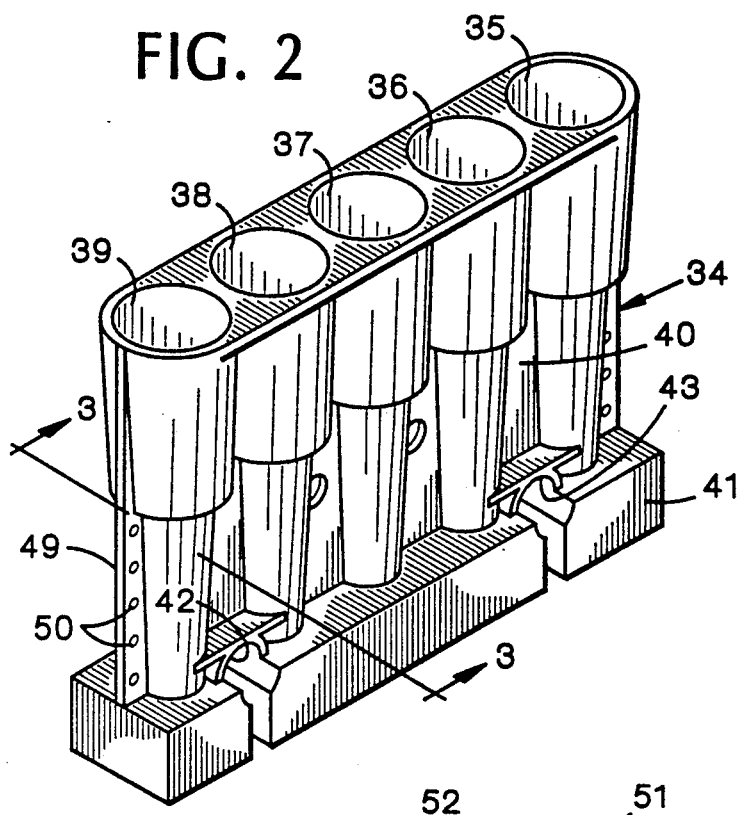

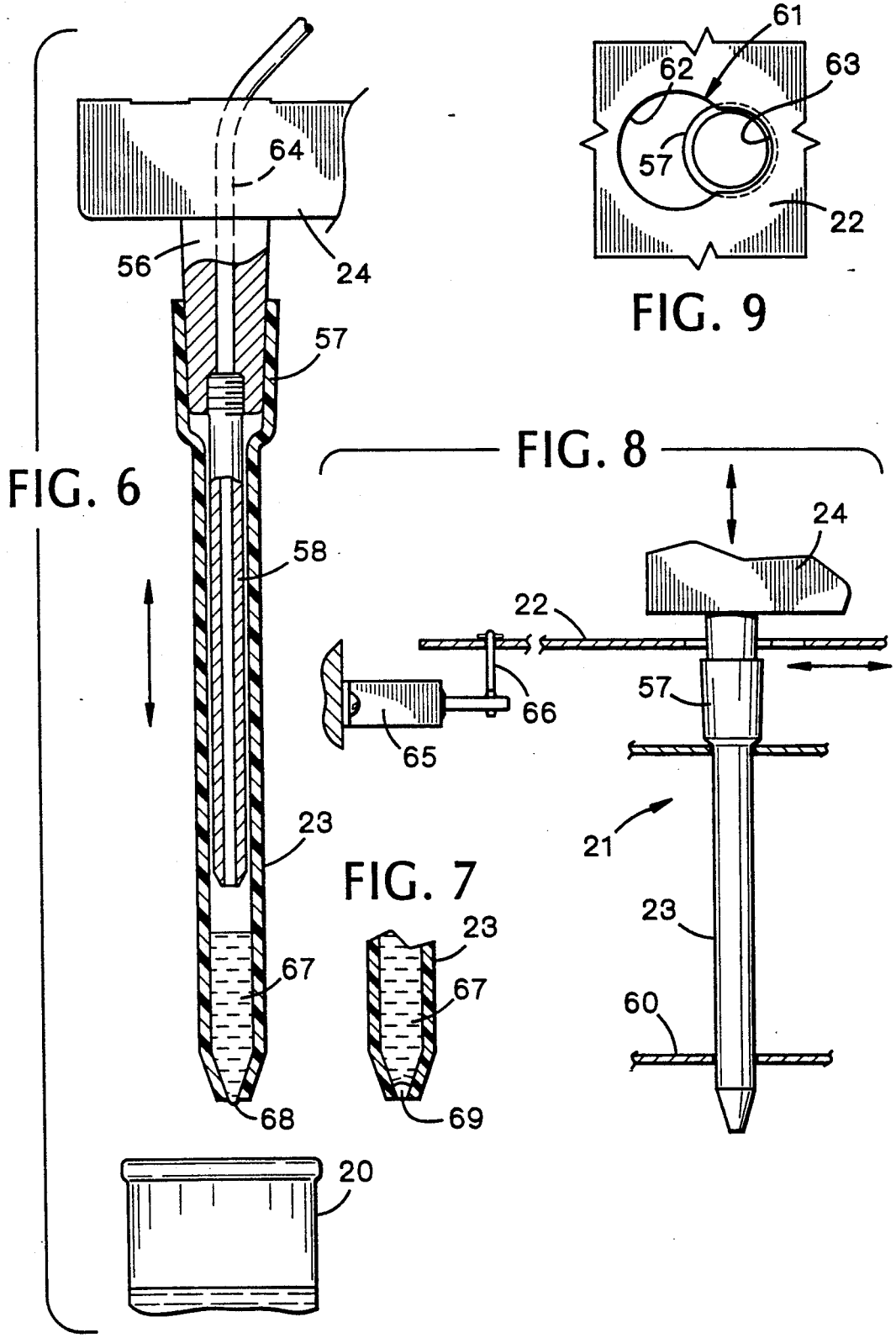

METHOD AND APPARATUS FOR EFFECTING SOLID PHASE EXTRACTION

CROSS-REFERENCE TO RELATED APPLICATION

The present application is a division of U.S. application Ser. No. 07/158,902, filed Feb. 22, 1988, abandoned.

FIELD OF THE INVENTION

This invention relates to the analytical separation of compounds one from another and, more particularly, relates to a new and improved method and apparatus for accomplishing solid phase extraction.

BACKGROUND OF THE INVENTION

U.S. Pat. No. 3,966,410 basically describes an analytical separation method known as solid phase extraction.

In the solid phase extraction system, one provides an elongated generally cylindrical tube having an inert chemically non-reactive packing material therein, which has a large surface-to-volume ratio, and a small lower outlet in the form of a nozzle. A liquid sample is introduced into the tube through an upper input end. When the sample reaches the packing material, it spreads out as a thin liquid film with a large surface of the packing material and forms thereon in a stationary state. The primary function of the packing material is to provide a large surface area over which the sample spreads out as thin liquid film, without reacting wiht the packing material. The entire sample remains on the packing material as a thin liquid film, so long as no other matter is introduced into the tube. To extract a compound or a family of compounds from the thinly spread out sample, a solvent system is introduced into the tube. The term "solvent system" refers to a solution of a solvent or solvents which is immiscible in the original sample liquid and one or more reagents selected on the basis of the desired extract. This solvent system, commonly referred to as an "eluate", is utilized to elute (liberate) out the compounds of interest from the sample.

As the eluate passes through the packing material, it comes in contact with the thinly spread out sample over the very large surface area and intimate contact between the sample and the solvent system is achieved. The reagents are chosen to cause the partition coefficients of only the desired compounds to be extracted to change in favor of the eluate. Thus as the eluate comes in contact with the spread out sample, the desired compounds become dissolved in the eluate and exit therewith as the desired extract. This extract is known as the "eluent". The last of the compounds in the sample remain dissolved in the sample liquid and remain in a stationary state on the packing material. After extracting on extract, a subsequent extract consisting of a different family of compounds may be extracted from the remaining sample by passing a second eluate through the tube. The second eluate causes the partitions of coefficients of the compounds to be included in the second extract and second eluent. This process may continue with different eluates until the subject of the investigation is isolated in the packing, and may further be utilized to detemine from the various eluents what has been extracted.

The packing materials may include cellulose fibrous materials, such as absorbent cotton, filter paper, and multi-layered pressed alpha-cellulose sheets, glass fiber materials such as glass wool or pyrex wool and silica sand or gel in a powdered or fine granular form. The packing material used should be of high purity so as not to contaminate the sample and posses a high degree of absorbency in order to absorb and thereby retain the sample therein in a stationary state. Moreover, it should have a high ratio of surface area to volume so as to enable the sample to spread out as a thin film over the packing material surface and enable the eluate to pass therethrough.

The eluates are chosen to change the partition coefficient of the compounds to be extracted from the sample in favor of the eluate. Therefore, the desired compounds or the sample separates from the sample and become dissolved in the eluate. The packing material is practically saturated by the sample and therefore none of the eluate is retained by the packing material, and also therefore, the eluent flows through the packing material and exits the tube through the lower nozzle end.

In this solid phase extraction process, the pH of the sample may be adjusted to change the partition coefficient in a direction to enable the compound(s) to be extracted to become soluble in the eluate.

The solid phase extraction technique may investigate liquid samples such as blood, urine, bile, stomach content, homogenized tissue, liquid or liquified foods and beverages, waste water or water for human and animal consumption, and industrial preparations, only by way of example. The chemical compounds contained in such liquid samples may be drugs and drug metabolites, hormones, lipids, metabolites, normal or abnormal body metabolites, hormones, lipids, vitamins, poisons and contaminants useful and deleterious. The elutes may be any materials which may be utilized to remove compounds from the samples in an attempt to isolate a substance under investigation.

The solid phase extraction process is considered to be an improvement or an alternative to what is known as the "liquid-to-liquid" extraction process, which is also described in U.S. Pat. No. 3,966,410.

Besides the solid phase extraction process described above, there are a number of processes that separate compounds one from another. These processes range from simple filtration methods to complex extraction procedures. In even the relatively simple filtration methods where components are separated on the basis of size, such processes can become complex within a large variety of filter media available. Extraction procedures range from simple methods where a compound is washed with only one solvent or elute, up to complex methods with a variety of solvents or elutes in a sequential manner. In general, all these methods involve the use of some type of container to which the sample under study is added. The container will have some method of holding or supporting the samples, where it is subjected to the flow of additional eluates, and a means as necessary to collect the eluent. The solvents or eluates are normally liquid and require some method of forcing them through the sample and the filtering means. While gravity is always available, this is a slow process and usually either pressure or vacuum is required to overcome the frictional flow losses in the support medium. These separation techniques might further be subdivided into different categories. One category is where different samples or eluates are passed through a reusable substrate to obtain separation. An example of this is high performance liquid chromatography (HPLC) where the passage of the sample through the column achieves the desired separation. One eluate after another is passed through the same column. To hasten this type of process, it is only necessary to provide a means of injecting the various eluates into the column.

All of these known processes of separation are primarily quite time consuming, and are primarily manually accomplished.

Accordingly, the present invention is directed to separation techniques in which a virgin substrate is used for each separation, for example, where a filtration process requires a new filter medium between each sample. However, the silica gel or sand may be cleaned and reused. Due to the number of steps that may be required, these processes are usually manually performed. The means of adding solvents or catching eluates may be mechanized, but the changing of substrates between samples is usually done manually. While the method of processing an individual sample may be mechanized, the changeover from one sample to another requires manual interface.

Accordingly, the present invention provides a new and improved process and apparatus for speeding the processes for separating compounds for the analytical study of samples.

SUMMARY OF THE INVENTION

The invention utilizes a cassette defining a multiplicity of tubes which are used in analysis of various specimens. Each of the tubes of the cassette is packed with a substrate having upper and lower porous frits. The substrate, which may sometimes be referred to as the absorbent material, is selected in accordance with the material which is desired to isolate. The cassettes are transported to a first station where they are sequentially moved by a motor driven mechanism to a position below a specific nozzle which injects preconditioner into each tube to render the absorbent hydrophilic, so that subsequent liquids will not pass swiftly through the substrates. The preconditioning agents are then drawn by vacuum through the tubes and the substrate, but the vacuum is applied only until the level of the liquid preconditioning agent is slightly above the top frit, thus maintaining the wetted condition of the filter material. As the tubes of each cassette advance past the preconditioning points, they are injected with an exact amount or aliquot of the sample to be tested. The cassette is then released to a transfer mechanism which advances it to a second station while accepting another cassette and advancing it to the first station.

At the second station, the tubes of the cassette receive a predetermined quantity of a washing solution, which may be water, and subjected to pressure to move the water through the tube. At this time, the sample will be retained in the absorbent substrate. The purpose of the wash is to remove any contaminants from the substrate. This process is repeated in moving the first cassette to a third work station, while picking up a third cassette and moving it to the first work station. At the third station, an eluate which is a solvent for a substance under investigation is applied to the tubes of the cassette and forced through under pressure. The liquid exiting the tubes, referred to as the eluent, is collected in individual tubes in an eluent tube carrier or rack and is removed for investigation or other analytical processing.

Apparatus embodying the invention further comprises a fourth station to which the first cassette is moved, while a fourth cassette is moved into the first station. At this station, another eluate is added to each tube of the cassette and forced therethrough under pressure to receptacles which will collect the eluent. For example, if urine is the sample, the first eluate may be a substance which is a solvent for cocaine, and if present, the cocaine bearing solvent would be the first eluent. At the fourth station, the second eluate might be a solvent for amphetamines which would then remove any amphetamines from the sample into the second eluent.

When the cassettes have been completely acted upon, they are discarded and the eluent tube racks are then removed for analysis of the eluents.

In terms of structure, the cassettes are loaded in a cassette infeed magazine which is moved to a position to present a first cassette to a side-to-side transfer mechanism, where the cassette is inserted into this transfer mechanism and also on a main carriage which has front-to-back movement, as well as an elevator platform thereon. The main carriage with the first cassette thereon is indexed below a station where each tube receives a preconditioning agent to render absorbent material therein hydrophilic. The first cassette is positioned on a vacuum manifold member having a number of separate compartments equal in number to the number of tubes of the cassette. This occurs in what is referred to as channel A on the main carriage. A vacuum line is connected to each compartment and draws down the preconditioning liquid through the absorbent substrate. After presentation of the preconditioning agent, the main carriage is indexed forward to receive a liquid sample to be analyzed in each tube. Vacuum continues to be applied to each compartment of the vacuum manifold until the liquid level of each tube is at a predetermined height which is above the absorbent material. As the last tube is filled with a sample, the main carriage is in a forward position.

At this time, or at a time to be further described, two magazines are moved in from either side of the main carriage and behind the main carriage to present a rack carrying a plurality of eluent tubes to holders therefor on the instrument. These racks will subsequently be received in two channels designated C and D on the main carriage. The main elevator platform of the main carriage now moves down to disengage the pressure manifold from the first cassette and then moves backward below the presented racks and then upwardly to accept the racks into the two channels C and D. As the main carriage moves back to the rear position, the transfer mechanism moves to accept a second cassette for insertion in column A, and the transfer mechanism moves the first cassette to a position on the main carriage referred to as channel B. The main carriage then indexes outwardly toward the front, the second cassette is then operated upon as previously described for the first cassette, and the tubes of the first cassette are engaged by a pressure manifold. As the main carriage is indexed forward, the first cassette in passage is joined to a pressure manifold and the tubes thereof have applied thereto a washing liquid whose purpose is to remove compounds which have not bonded to the absorbent substrate. When the main carriage has indexed to the forward position, pressure is applied to the tubes of the second cassette and the washing liquid is forced through the substrates thereof.

Depending upon the sample to be analyzed, the washing step may be either used or omitted. Also optional is a step of blowing drying air or dry nitrogen through the tubes when the main carriage is in the forward position.

At this time, the eluent tube racks may be inserted as described in the second preceding paragraph, if not previously inserted. The cassette tubes have now been filled with a sample, washed and dried, if necessary. The main carriage is now moved back to a rear position, the first and second cassettes are moved by the transfer mechanism to a position to be accepted on columns B and C on the main carriage, and a new cassette is positioned at column A.

As the main carriage moves forward, a first eluate is injected into the tubes of the first cassette, the second and third cassettes are operated upon as previous described. The eluate in column C is a solvent which will remove a suspected compound in the absorbent material into the eluent tubes in an eluent rack.

The main carriage is then moved back, the transfer mechanism will pick up a fourth cassette from the cassette infeed magazine and transfer the first cassette from column C to column D. In both of columns C and D, the eluate will be applied through the absorbent substrate to pick up substances in the absorbent substrate.

After four cassettes have been acted upon, the eluent outfeed magazine racks in channels C and D move in to extract the eluent racks from channels C and D, and the process continuously repeats.

The features of the invention which are believed to be novel are particularly pointed out and distinctly claimed in the concluding portion of the specification. The invention, however, together with further objects and advantages thereof, may best be appreciated by reference to the following detailed description taken in conjunction with the drawings.

BRIEF DESCRIPTION OF THE DRAWINGS

FIG. 2 is an isometric view of a cassette utilized in practice of the invention, exemplified as having five tubes;

FIG. 3 is a view seen in the plane of lines 3—3 of FIG. 2;

FIG. 4 is a view similar to FIG. 3, but showing a different tube substrate arrangement;

FIG. 5 is an isometric view of a rack for holding tubes which accept an eluent from a cassette as shown in FIG. 2;

FIG. 6 is an elevation partially in section of an aspirating arm with an aspirating tip thereon;

FIG. 7 is a fragmentary view of a portion of FIG. 6;

FIG. 8 is a view partially in section of an aspirating tip magazine which holds the aspirating tips as exemplified in FIG. 6;

FIG. 9 is a fragmentary view of a stripper plate used to remove an aspirating tip from the aspirating arm of FIG. 6;

DETAILED DESCRIPTION OF THE PREFERRED EMBODIMENT OF THE INVENTION

Figure 1:
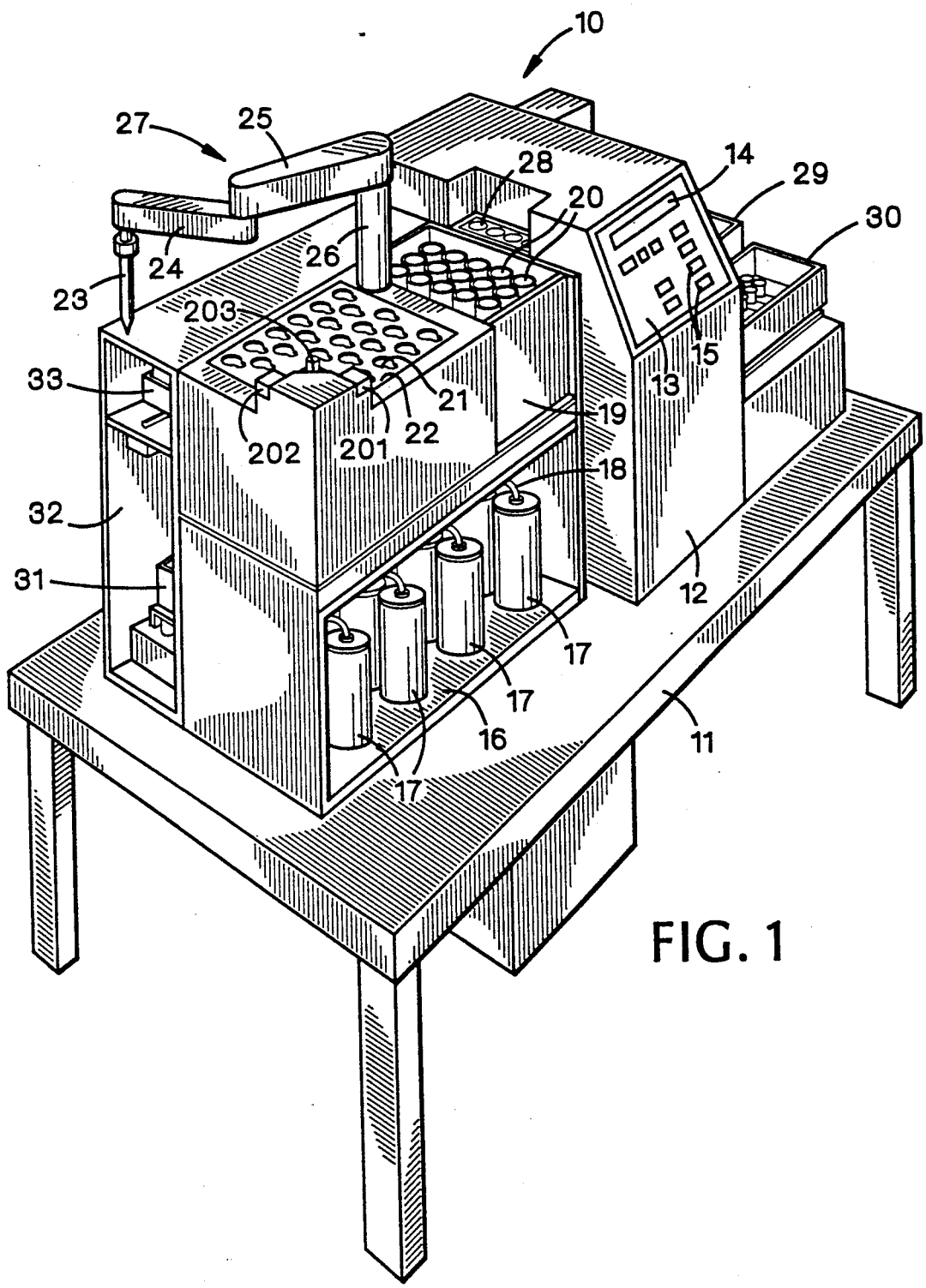
FIG. 1 is an isometric view of apparatus embodying the invention.

An instrument 10 embodying the invention is mounted on a table or support 11 therefor and comprises a first housing member 12 having a display panel 13 thereon, which may include a readout device 14 and depressible buttons 15, which will actuate switches to call for a given sequence of operation. A compartment 16 is provided to house a plurality of reagent or eluate containers 17. The containers 17 have liquid lines 18 extending therefrom to a manifold plate, hereinafter described. Supported on housing member 12 is a rack or container 19 for tubes 20 containing aspiration tips, as hereinafter described. The magazine 21 further includes a stripper plate 22 to strip aspiration tips from an aspiration nozzle. As shown in FIG. 1, an aspiration tip 23 is fitted to an aspiration nozzle. The aspiration nozzle depends from a pivotal elbow 24. Elbow 24 is pivotal with respect to an arm 25 on a column 26. Column 26 has both rotary and vertical motion. Three motors TLM, TSM and TAM are provided for vertical movement of column 26, rotary movement of column 26 and rotary movement of elbow 24. The purpose of the arms 24, 25, and 26 which hereinafter collectively are referred to as the sample arm 27 is to position an aspiration tip over one of sample tubes 20, then to descend into a sample tube, aspirate a given quantity of the sample and transfer the sample to a cassette at a sample loading station 28.

The apparatus further comprises eluent outfeed magazines 29 and 30 which will pick up and load racks containing tubes of eluent. The instrument 10 further includes a first infeed magazine 31 for infeeding racks of eluent tubes in a compartment 32, and an upper magazine of cassettes 33. A second magazine (not shown in FIG. 1) is also provided in infeed racks of eluent tubes.

Reference is briefly made to FIGS. 2, 3, 4, and 5, which illustrate a cassette 34 utilized in and embodying the invention. The cassette 34 is a molded one piece structure having distinct areas or tubes 35, 36, 37, 38, and 39, with interconnecting webs 40 and a generally rectangular base 41, to permit upright support 9. The base is defined by walls which provide a hollow interior. The cassettes define two guide passages 42 and 43 for receiving rod-like support members, as hereinafter described. The passages 42 and 43 are partially defined in base member 41, and the base member 41 has openings therein extending from passages 42 and 43 through base member 41. The cassettes are arranged to be filled and a substrate or an absorbent material 44 as previously defined, between upper and lower porous frits 45 and 46, respectively. The lower portions of the tubes are slightly frustro-conical and receive the frits in a very tight or press fit. As shown in FIG. 3, each of the tubes 36-39 terminate at its bottom in a Luer nozzle fitting 47 within base 41. FIG. 4 exemplifies a modified form of the invention where a column member 48 is inserted in the lower portion of a tube 35 to decrease the amount of absorbent or substrate material 46, which is utilized and maintain a predetermined height to width proportion which may be required by a process.

The tubes 35–39 have vertical axes as the cassettes are moved through the system, and the guide passages extend through the cassette essentially perpendicular to the vertical axes of the tubes. As shown, the passages are partially defined in the rectangular base member. The base member has walls defining a hollow interior and lower edges. The nozzle 47 ends of the tubes 35–39 extend into the hollow interior of base member 41 and terminate above the lower edges thereof.

The cassette further includes ribs 49 on the extremities with small recesses 50 therein to permit binary encoding of each cassette.

The cassette 34 is designed to be processed automatically. The guide openings 42 and 43 allow it to be positioned precisely at various stations through the instrument. The separation material exemplified by the reference numeral 44 may be as simple as a filter that separates according to size, or it may be a sophisticated solid phase medium that separates on the basis of partition coefficients. The separation media may be a filter pad, supported within the container tubes or as shown, it may be a powder trapped by the two porous retaining frits. The top of each tube is open to allow the introduction of samples and reagents. The Luer type nozzle permits automatic connection to another receptacle.

FIG. 5 illustrates a rack 51 having receptacles arranged to receive five eluent tubes 52 (only one shown). Racks 51 have two pin locating recesses 53 extending into the bottom thereof and have upper and lower pairs of recesses 54 and 55 on either sides thereof to enable handling thereof as hereinafter described.

Reference is now made to FIG. 6 which shows an aspirating tip mounted on a nipple-like member 56 which depends from arm 24. The nipple-like member 56 is tapered as is the interior surface of the upper portion 57 of tip 23. When the nipple-like portion 56 is inserted into a portion 57 of a tip, there is frictional engagement. A nozzle 58 is joined to member 56 and extends downwardly therefrom into a tip 23. Consider now also FIG. 8, which exemplifies aspirating tip magazine 21. The tips 23 are supported below portion 57 on a plate 59 and also extend through apertures in an alignment plate 60. Stripper plate 22 has a plurality of apertures defined therein in a generally keyhole shape 61. Such keyhole shape includes a portion formed on a large diameter 62 and a portion formed on a smaller diameter 63. Large diameter 62 is of sufficient size so that a tip 23 may completely pass therethrough. However, if the stripper plate 22 is moved to a position as shown in FIG. 9 and sample arm 27 is raised, the tip 23 will be stripped from member 56 as plate 22 overlies upper portion 57 of the tip. The operation is such that the sample arm will position vacuum nozzle 58 over a selected tip and then will move downwardly to cause a tip 23 to engage member 56 and will then raise the tip from the cartridge magazine and move to a position over one of sample tubes 20. A passage 64 through arm 24 leads to a vacuum pump which will aspirate a precise amount of fluid of a sample into the tip 23. As shown in FIG. 6, the tip is moving upwardly from a sample tube 20 and the liquid 67 therein forms a small meniscus 68 which may drop from the tip. Therefore, as the sample arm raises to a predetermined position which is clear of a sample tube 20, there will be a short pulse in the vacuum to draw the liquid 67 slightly within tip 23 and leave a small air pocked 69. Each tip 23 is used with only one sample in a tube 20. If another sample is to be utilized in a cassette, the tip is stripped to its home position, and a virgin tip 23 is picked up for each distinct sample. The tips 23 are reusable only with the same sample previously aspirated.

Figure 10:
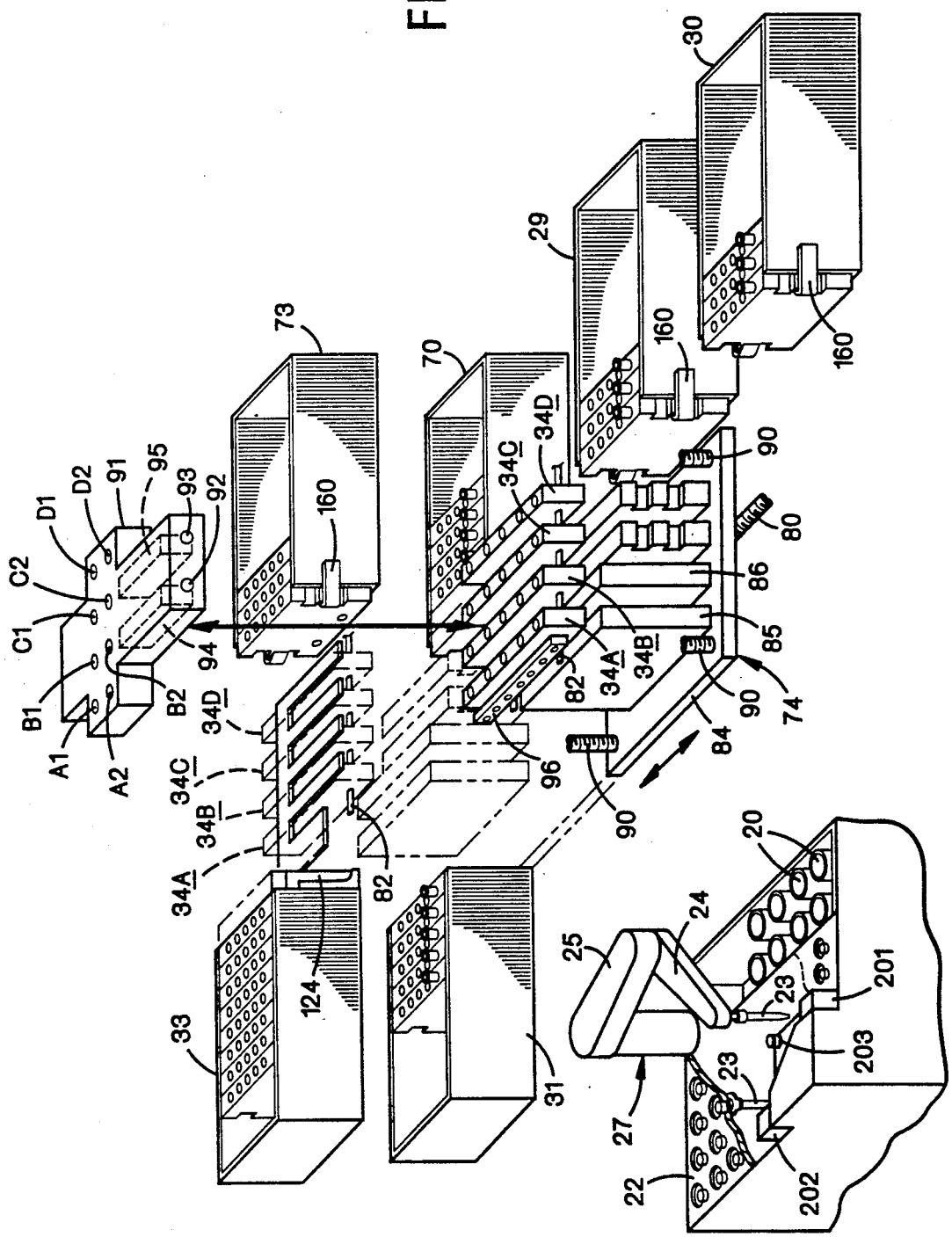
FIG. 10 shows the cassettes with magazines and carriage mechanism including elevator platform of the system.
Figure 11:
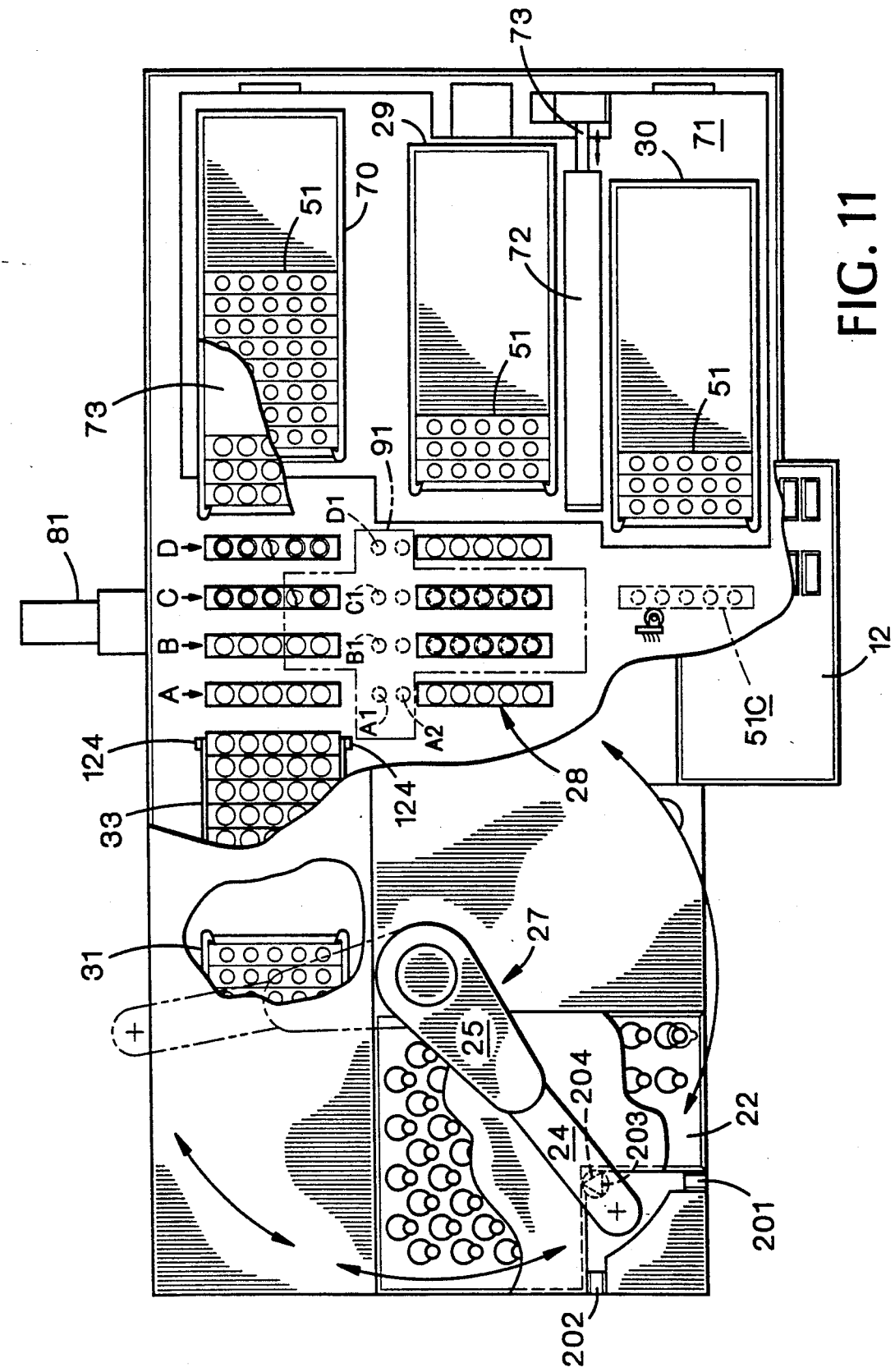
FIG. 11 is at top plan view of the apparatus of FIG. 1 with covers partially removed.

Reference is now made to FIGS. 10 and 11. FIG. 11 shows a second magazine or tray 70 for infeeding racks 51 containing eluent receiving tubes 51. Magazines 29, 30, and 70 are mounted on a slide 71 driven by the piston rod 71 of a cylinder 71. FIG. 11 also shows, in part, a spent cassette outfeed magazine 73.

In FIG. 11, the areas upon which the substance in the cassettes is acted upon are labeled columns A, B, C, and D. In operation, all of the cassette and eluent tube magazines will move at the same time. Cassette magazine 33 will present a cassette 34 to a transfer and as the transfer mechanism moves the cassette to channel A, it will move the cassette at channel D into spent-cassette magazine 73. The cassettes are above the eluent tubes and eluent tube magazines move in to deposit racks 51 on holders in channels C and D. Also, at this time, magazines 29 and 30 move in to pick up racks 51 from channels C and D. The eluent tube racks in operation are carried on a main carriage 74 which moves horizontally and vertically. Magazine 29 will pick up the rack from channel d. The rack in channel C will be advanced on main carriage 74 to the position shown as 51c in FIG. 11, where it can be picked up. At this point, main carriage 74 is in a forward position as shown in full line in FIG. 10. Carriage 74 is moveable in the horizontal on a lead screw 80 driven by a motor 81.

As shown in FIG. 10, the cassettes are transferred from magazine 33 to a pair of support rods 82 (only one shown) in FIG. 10. These support rods extend through the openings 42 and 43 in the cassettes. The rods 82 are mounted on main carriage 74 as will hereinafter be exemplified.

The cassettes are indexed between the cassette infeed magazine 33 to the spent-cassette magazine 73 by a walking beam construction hereinafter described. The carriage 74 includes an elevator platform 84 which carries thereon a vacuum manifold 85, a pressure manifold 86 hereinafter described, as well as two removable racks 51. Elevator platform 84 is movable vertically on four lead screws 90 (only three shown) in FIG. 10.

The apparatus 10 also includes an upper manifold plate 91 which is shown in dotted line in FIG. 11. Manifold plate 91 has four rows of two through passages therein identified by the reference A, B, C, and D followed by an arabic numeral. These passages are connected to the reagent containers 17 shown in FIG. 1 via the piping 18 and intermediate the connections are pumps and solenoid valves hereinafter described. Also defined in manifold plate 91 are passages 92 and 93 leading to manifolds 94 and 95 respectively. These manifolds are utilized to blow air or dry nitrogen through the cassettes when the cassettes are in channels C and D for drying purposes.

Also provided is a member 96 as shown in FIG. 10 and more fully explained hereinafter which is positioned on carriage 74 with respect to each cassette in channel A to sense the level of liquid in each cassette tube and to prevent draw down of liquid through the frits and substrate beyond a predetermined level.

To exemplify the transportation and movement of a cassette through the system reference is made to FIG. 10. The cassette positions will be identified as 34a-34d, and 34a'-34d'. A cassette is first transferred from infeed magazine 33 to the position 34a, at which time it is picked up by carriage 74 on rods 82. It is then indexed to the position known as 34a, at which time it passes below two nozzles in manifold plate 91. The carriage 74 then moves the cassette indicated at position 34a to position 34a in a stepwise motion, and each tube of the cassette receives an aliquot of a preconditioning agent beneath nozzles in passages A1 and A2. The preconditioning agent may be the same beneath both of the nozzles.

As the cassettes are indexed from the rear position shown in FIG. 10 to the forward position on carriage 74, they pass beneath the nozzles in each of columns A, B, C, and D. At each position in a column, each tube of a cassette receives a predetermined aliquot of a preconditioning agent to render the substrate hydrophilic. It would be possible to use only one nozzle in each of columns A, B, C, and D. However, the feed is set for a predetermined amount of liquid, and if this is not sufficient, then additional liquid is applied at the second nozzle. For example, each nozzle may inject five milliliters of the preconditioning agent to render the substrate hydrophilic. As each tube of the cassette has the preconditioning liquid applied thereto, it advances to the location shown at 28 in FIG. 1, and sample arm 27 through tip 23 will apply a predetermined aliquot of a sample to each tube. When all of the tubes of cassette 34a have had the preconditioning agent and the sample applied thereto carriage 74 is then moved back to the position shown in FIG. 10. However, at this time, the walking beam mechanism has been advanced to the left as viewed in FIG. 10 and the preconditioned cassette goes to location 34b. When carriage 74 again comes forward, it moves to position 34b. Thereafter it is moved through positions 34c, 34c', 34d, 34d', and then off loaded into the spent-cassette magazine.

In column A each tube of a cassette has the preconditioning agent and sample subjected to a vacuum to pull these substances through the substrate, and the sample is absorbed by the substrate after it is rendered hydrophilic by the preconditioning agent. A typical preconditioning agent is methyl alcohol (methanol). In channel B the sample receives a washing solution to remove any possible contaminants which have not been absorbed by the substrate 44. This washing solution is forced through the cassette tubes under pressure. At channel C the first eluate is introduced as a solvent for removal of a first compound from the absorbent material and forced under pressure into the tubes 52 in a first eluent tube rack. At column D a second eluate as a solvent for removal of a second compound from the absorbent material is introduced and forced under pressure into the tubes 52 in a rack 51.

Figure 13:
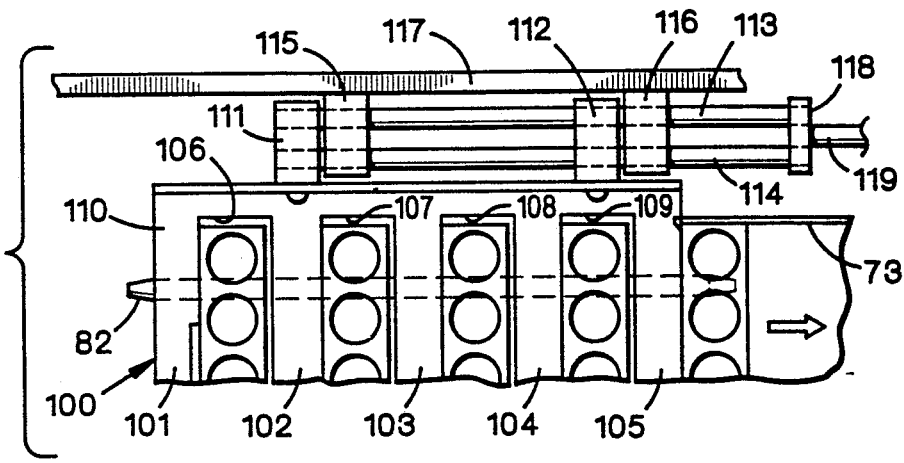
FIG. 13 is a view of a portion of FIG. 12.
Figure 12:
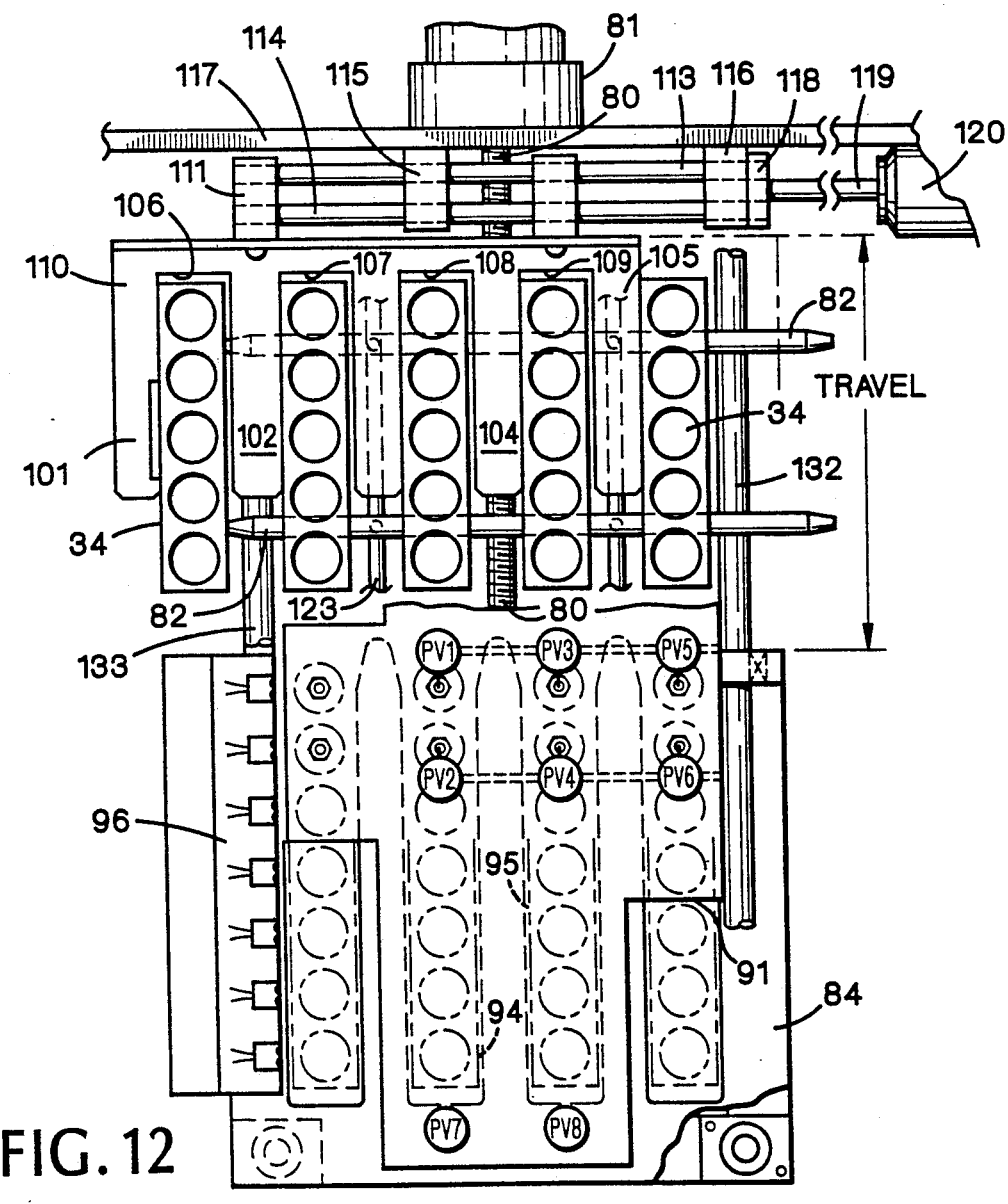
FIG. 12 is an enlarged plan view of a portion of FIG. 10, showing more detail.

Reference is now made to FIGS. 12 and 13. The walking beam construction 100 as shown in FIGS. 12 and 13 comprises a member having five fingers 101, 102, 103, 104, and 105, defining cassette receiving recesses 106, 107, 108, and 109, therebetween. All of the fingers are joined into a common end member 110 which is affixed to two side blocks 111 and 112 slidable on rods 113 and 114. The rods are carried in guide blocks 115 and 116 which are affixed to the back wall 117 of housing member 12. The rods 113 and 114 are affixed to a common member 118 which is attached to a piston rod 119 of an air cylinder 120.

Piston 120 when energized will move waling beam 100 a predetermined dimension in either direction. This predetermined direction is selected to move a cassette between two fingers in the walking beam a predetermined amount to register with one of channels A, B, C, and D. In this manner, each cassette as it is taken from infeed cassette magazine 33 will first move to position 34a as shown in FIG. 10, then the carriage 74 will move cassette 34a to the position shown at 34a. Then the walking beam 100 will move to pick up another cassette. At this time, the cassette at position 34a will be moved by carriage 74 into position 34b. Then the walking beam 100 will return to the right as shown in FIG. 13 and thereafter the original cassette shown at position 34a will be moved by carriage to position 34b and a new cassette is at position 34a in channel A. This will continue until a cassette has advanced to positions 34b, 34c, 34c, 34d, 34d, and then will be loaded in the spent cassette magazine 70. There will be alternate motion of the walking beam 100 to the left and right as viewed in FIG. 13.

As shown in FIG. 12, walking beam 100 is in a position to accept a new cassette prior to column A. It is also in a position to deliver a cassette in column D to spent-cassette magazine when it moves back to the position shown in FIG. 113. As shown in FIG. 13, finger 105 has pushed a cassette from column D into spent-cassette magazine 73.

The guide rods 82 are mounted on the carriage 74 and will move therewith, as hereinafter pointed out.

Thus, when the walking beam is in its left most position as the carriage returns toward the back wall 117 of the housing, the cassette will be introduced into the next recess between the fingers 101-105 of the walking beam, so that when the walking beam 100 again moves to the right, it will be aligned with a next succeeding column with respect to carriage 74.

Figure 14:
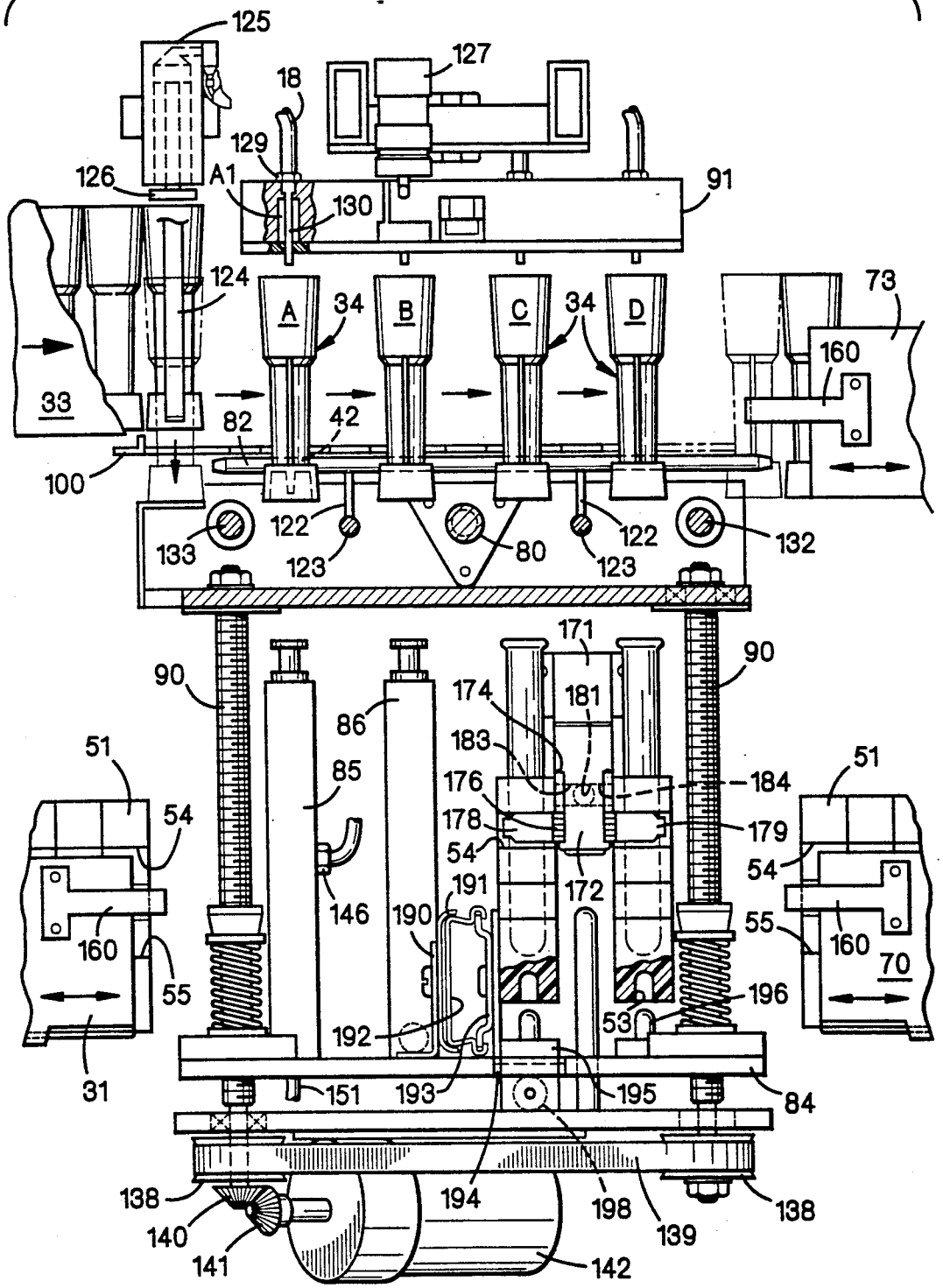
FIG. 14 is a front elevation of the apparatus of FIG. 12.

The rods 82 are supported on carriage 74 on post-like members 122 (FIG. 14) extending upwardly from lower rods 123 supported on main carriage 74. When a cassette is loaded into the walking beam, the walking beam is in its left-most position as shown in FIG. 14. The cassettes in the cassette infeed magazine 33 are held in a walking beam loading position by spring arms 124 on either side of magazine 33. An air actuated cylinder 125 has a piston 126 which will engage the top of a cassette and stroke it to the position shown in broken line in FIG. 14. Then, when the cylinder 120 returns walking beam 100 to the right, passages 42 and 43 in the cassette accept the rods 82.

Disposed above the channels A, B, C, and D on carriage 74, as shown in FIGS. 10 and 11, is fluid manifold 91. Manifold 91 is movable between an upper position, as shown in FIG. 14, to a lower position as shown in FIG. 15 by air cylinders 127 carried on a bracket 128 affixed to the back wall 117 of housing 12.

As shown in FIG. 14 as exemplified by opening A1, each of the openings A1, A2, B1, B2, C1, C2, D1, and D2, receives a fitting 129 to which is connected a line 18 from one of the reagent containers 17. The fitting includes a downwardly directed nozzle 130, which will inject a predetermined quantity of a preconditioning reagent in channel A into each tube of a cassette 34, as the cassette is stepped beneath manifold plate 91. The reason for introducing the preconditioning reagent and other liquids at two points is to enable a larger amount of liquid to be added to a tube and reduce the size of the cassettes. If the cassettes were made larger, this would necessitate a larger size overall instrument, only one injection nozzle per column could be utilized.

Figure 15:
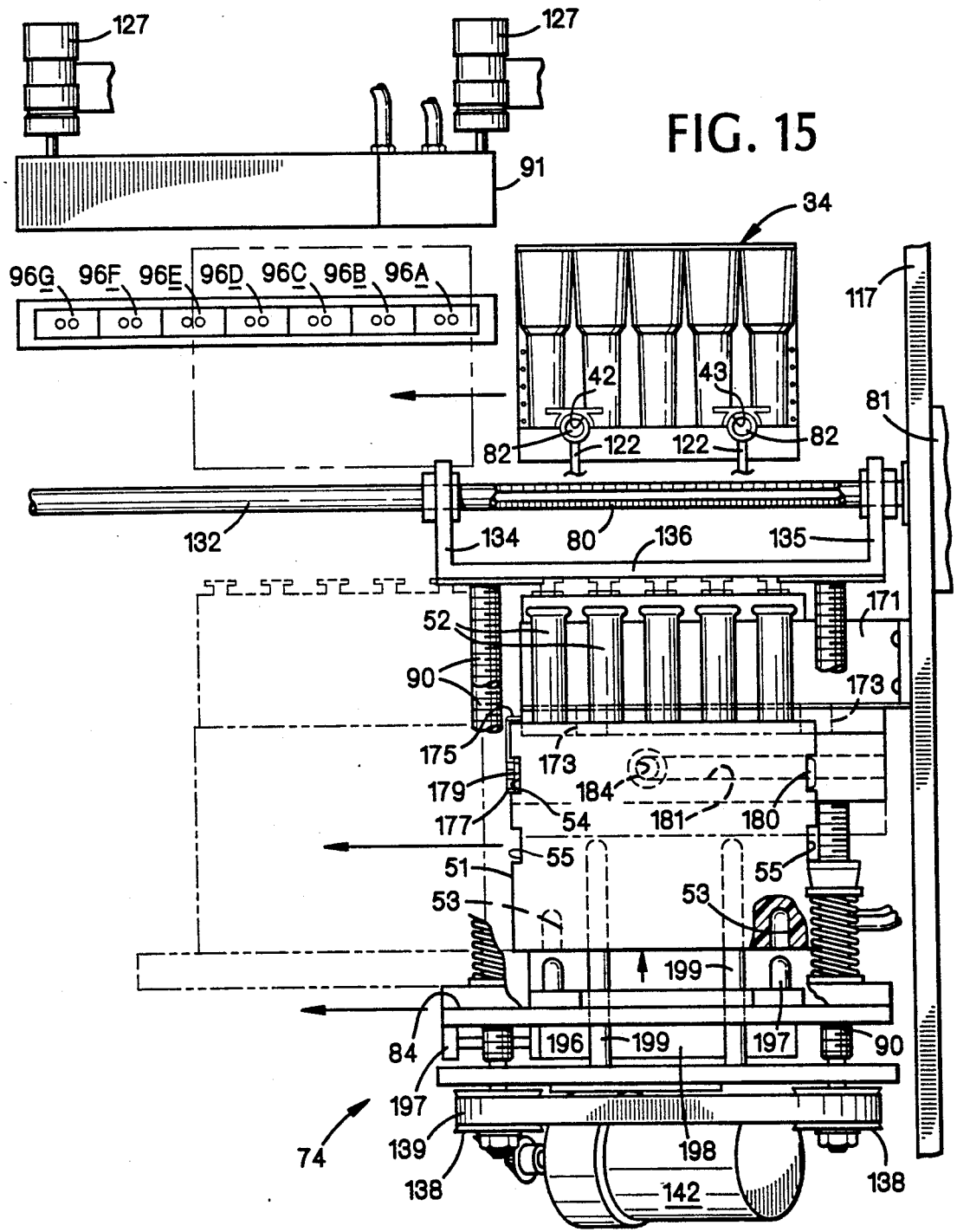
FIG. 15 is a side elevation of the apparatus of FIG. 14 seen from the right hand side thereof.

As shown in FIG. 15, a cassette is advanced by lead screw 80 on main carriage 74. The main carriage 74 is supported on guide rods 132 and 133 extending through upright arms 134 and 135 on an upper carriage member 136. Rods 123 are also supported at either end on arms 124 and 135. Elevator platform 84 moves upwardly with respect to carriage 74 on lead screws 90. All of the lead screws have affixed thereto pulleys 138, which are engaged by a pulley belt 139. One of the pulleys 138, which are engaged by a pulley belt 139. One of the pulleys, as exemplified in FIG. 14, has on the lower end thereof a bevel gear 140 which is driven by a bevel gear 141 on the shaft of a motor 142, which is supported on a base member 143 of carriage 74. When motor 142 is energized, and dependent on the direction of energization, it will raise or lower elevator platform 84.

Referring to FIG. 15, as a cassette 24 is indexed beneath manifold plate 91, it will pass a row of photo detectors 26a-96a which will detect whether the fluid in the tubes of the cassette are below a predetermined level, namely, a meniscus on top of the upper frit 45 in each tube. As will hereinafter be explained, in column A the Luer nozzle 47 of each tube of a cassette 34 is engaged by a fitting of a five compartment vacuum manifold 85 and a vacuum is applied thereto to draw the preconditioning reagent through the substrate of each tube. If the liquid in each tube falls below this predetermined level, the vacuum will be removed.

Figure 16:
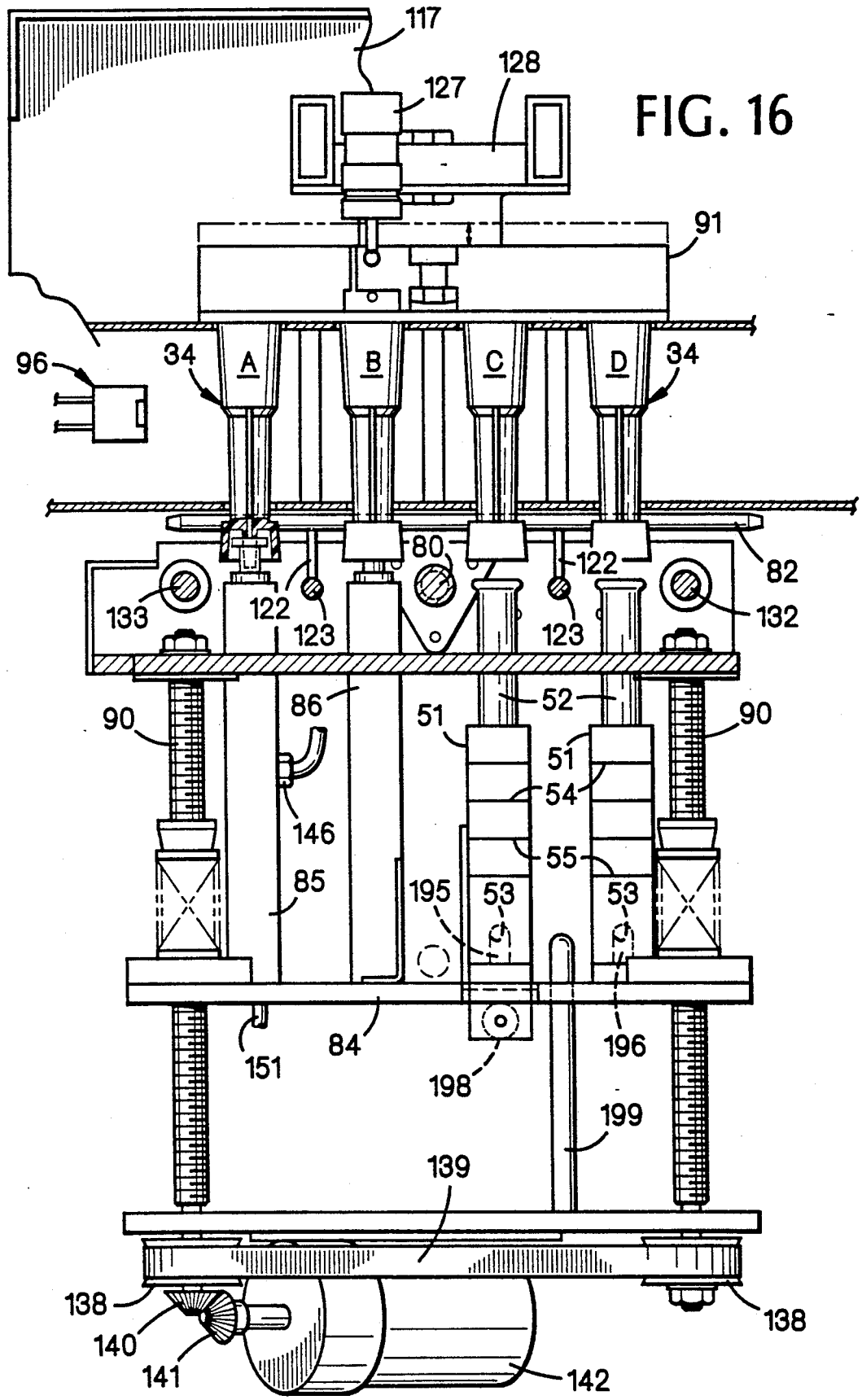
FIG. 16 is a view similar to FIG. 14, but with the parts in a different position.

As shown in FIG. 16, elevator platform 84 has raised vacuum manifold 85 to a position where a fitting 45 of one of the vacuum chambers has engaged a Luer nozzle 47.

Figures 17, 18:
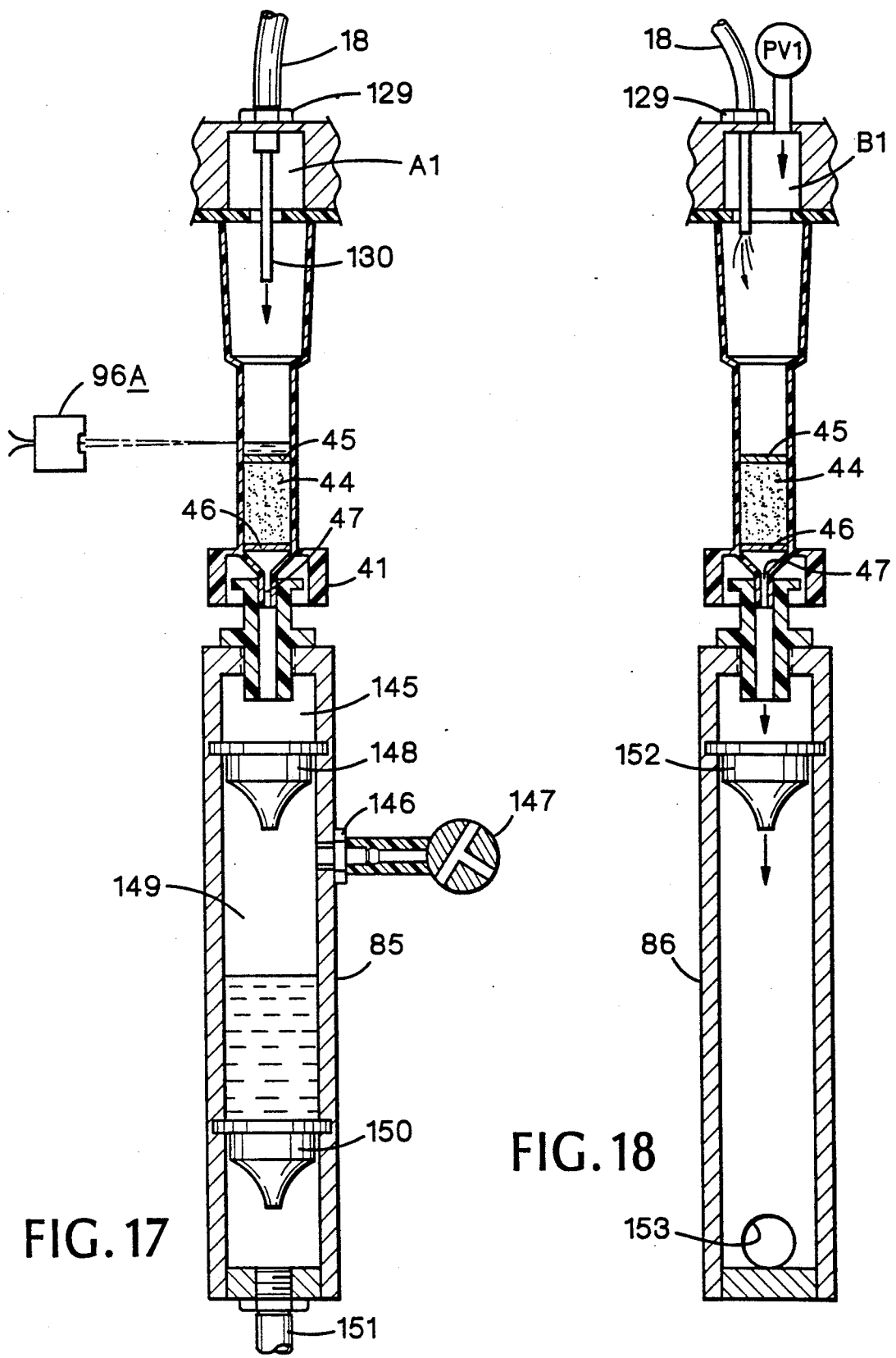
FIG. 17 is an enlarged end elevation, in section, of another station of the mechanism of FIG. 8.

Reference is now made to FIG. 17 which is a vertical sectional view through a cassette 24 and vacuum manifold 85, and manifold plate 91 at passage A1.

It will be understood that there will be a plurality of separate vacuum chambers 145 equal in number to the number of tubes on a cassette. Each compartment of vacuum manifold 85 has a fitting 146 extending to a valve 147. At the first station in column A, the preconditioning reagent is injected into the first tube through a nozzle 130, and a vacuum is applied via valve 147 into chamber 145. This will cause the fluid injected into the tube to flow through the substrate and through a duckbill valve 148 into portion 149 of chamber 145. A photo detector 96a will detect when the liquid has been drawn down to the predetermined level at the top of frit 45 and then the vacuum will be removed. The liquid drawn through the substrate will collect above a second check valve 150.

When sensor 96a senses the meniscus above frit 43, valve 147 is moved to the pressure relief position and vacuum to fitting 146 is terminated. Then, when all tubes have received the preconditioning agents and the sample from sample arm 27 via a tip 23, valves 147 are turned to the pressure position to force the liquid to exit through second duckbill valve 150 and exit through drain 151.

FIG. 18 is a vertical section through manifold 86 on elevator platform 84. Assume that the cassette of FIG. 17 has been advanced from column A to column B. Here in column B as the cassettes advance beneath the passages B1 and B2, a washing solution is introduced, through tube 18 and after the washing solution has been introduced, air pressure is applied through a solenoid valve PV1 and the washing solution is forced through substrate 44 and through another duckbill valve 152 and then exits through a drain 153. The cassette in column B, as exemplified in FIG. 18, will now be advanced one position and the operation will be repeated and then pressure solenoid valve PV2 (FIG. 12) is opened to blow the washing solution through the substrate into manifold 86.

When a cassette has indexed all the way in column B, as shown in broken line in FIG. 12, there is communication in the manifold 94 (FIG. 10) to all the tubes of a cassette, and drying air or nitrogen may be introduced to all the tubes of a cassette through a solenoid valve PV7. The same drying operation may be accomplished on the cassettes in column C through a solenoid valve PV8.

Referring to FIGS. 10 and 11, the eluent rack magazines 31 and 70 are arranged to feed eluent tube racks to channels C and D. Referring to FIG. 15, these racks 51 in magazines 31 and 70 are shown without the tubes 51 therein. On either side of the open ends of the racks are affixed grasping arms 160, which are turned over to the grasp rack 51. These arms are resilient and will release a rack 51, as will hereinafter be described. They will also accept a rack 51 pushed therebetween.

These arms are also provided on outfeed magazines 28 and 29 and may engage a rack from channels C and D, then remove the rack therefrom after engagement.

To explain the manner in which the racks for the eluent tubes are loaded and unloaded, reference is made to FIGS. 14 and 15. In FIG. 14, an extractor mechanism 170 is shown which comprises an upper stationary member 171 affixed to back wall 117. Extractor member 171 extends through columns C and D on carriage 74. A lower extractor member 172 is movable with respect to member 171 on pins 173 shown in broken line in FIG. 15.

Lower extractor member 172 moves a fixed distance in both vertical directions under drive by an air cylinder, as hereinafter described. Lower extractor member 172 carries a part of pins 174 and 175 with springs 176 and 177, respectively, thereon. Attached to the pins at the end shown in FIG. 14, are fingers 178 and 179 adapted to be received in recesses 54 of the eluent tube racks 51. The fingers 178 and 179 fitting into the recesses 53 will provide vertical support for the racks 50. At the other end of lower extractor member 172 are other arms 180 extending from either side thereof adapted to engage in the mating recess 54 of an eluent tube rack 51 at the other end thereof.

Also defined in lower extractor member 172 is a longitudinal port 181 connectable to a vacuum source which, at the end thereof, has ports 183 and 184 which will contact the racks 51 on either side thereof.

With reference to FIG. 11, it will be noted that the column C eluent rack 51c is advanced on elevator platform 84 of carriage 74 to a position where it may be picked up by eluent rack outfeed magazine 30. This is accomplished by a slide mechanism which comprises a bracket 190 mounted to the elevator platform and carrying a guide 191. Mounted within guide 191 is a slide comprising members 192 and 193 on a plate 194 attached to a block 195. Block 195 carries two locating pins 196 and 197 adapted to register with the locating recesses 52 in a eluent tube rack 51. slide 195 is driven by the piston 197 of an air cylinder 198 to the positions shown as 51c in FIG. 10. The purpose of this movement is to transport the eluent tube rack in column C to position 51c so it will be in a position for pickup by outfeed eluent rack magazine 30.

In operation, and at the same time, magazines 29 and 30 will be moved into positions to load eluent tube racks into channels C and D, respectively, while the main carriage 74 is in the position shown in full line in FIG. 10.

As the eluent tube magazines 70 and 71 come into position to present racks 50 to columns C and D, the arms 178 and 179, as well as arms 180 at the other ends thereof, will engage the presented racks 50 at the recesses 53, and will provide vertical support thereon under the overhanging ledges. Vacuum is then applied to line 181 and lower extractor member 172 will be coupled to the presented racks 50 from each of magazines 31 and 70. Then the magazines 31 and 70 are retracted by the vacuum will hold the extracted racks 51 in the position shown in FIGS. 14 and 15. Elevator platform 84 is then raised so that the locating pins 196 and 197 will engage in the recesses 52 in the base of racks 51. Then, the vacuum at passage 181 may be released. At this time, the eluent tube racks 50 in channels C and D are positioned on elevator platform 84. Upstanding pins or rods 199 are provided to prevent tipping of the racks 51 in the main carriage.

When the tubes in the eluent racks 51 in channels C and D have been filled, slide 194 is moved outwardly from platform 143 with the channel C eluent tube rack 50 thereon shown in FIG. 2. This is accomplished through the actions of cylinder 198 previously described.

At this time, slide 71 moves in carrying the eluent tube rack outfeed platforms 28 and 29 and the arms thereof will engage the racks 50 of the filled eluent tubes. Thereafter, elevator platform 84 is moved downwardly to free the locating pins 196 and 197 from locating recesses 52. Thereafter, the outfeed magazines on slide 71 are moved back with the racks of the filled eluent tubes. During this same operation, cassette magazine 73 picks up a spent cassette 24 as exemplified in FIGS. 10 and 11 from column D. The resilient arms 160 on the outfeed magazines 29, 30, and 73 will hold racks within the magazine and the same arms on the rack infeed magazines will release the racks 51 to the vacuum.

Reference is made to FIG. 11. When moving to deposit a sample in a cassette tube at station 28, sample arm 27 has arm 25 and elbow 24 in alignment and has moved from an extended position shown in broken line in FIG. 11 to the position shown in full line. In the position shown in full line, it is intermediate the paths of a photodetector 201 and a photo emitter 202 disposed at right angles to each other and both aimed at a prism 203 having a reflecting mirror 204 at 45 degrees to the beam of each of the photodetector and photo emitter. As arm 27 with a tip 23 thereon moves, its speed is known. When the tip is moved from the position shown in broken line through the beam and reflected beam of the photo emitter, two signals will be generated. The time between these two signals will be a measure of any angularity of the axis of an aspirating tip 23 with the axis of aspirating nozzle 58. This data is then utilized to calculate the position of elbow 24 when column 26 is lowered to insert an aspirating tube into a sample tube in sample container 19, and also at the tubes of a cassette at station 28.

In addition to the position sensors not specifically illustrated, the instrument contains the additional position sensors:

SRI—determines that the sample rack 19 is seated;
MCU—determines when the elevator platform 84 on main carriage 74 is up;
MCO—determines when the main carriage 74 is out as shown in full line in FIG. 10;
MCD—determines when the elevator platform 84 is down;
MMU—determines when the manifold plate 91 is up;
MMD—determines when the manifold plate 91 is down;
SLB—determines when slide 71 is back (to the right) as shown in FIG. 11;
SLF—determines when the slide 71 is forward;
CA1—determines that a cassette is in a position to be advanced in channel A;
CA2—determines when the cassette outfeed magazine is in a position to receive a spent cassette;
CA3—determines when the cassettes in magazine 33 have been expended;
EM1—determines when eluent rack magazine 31 is retracted;
EM2—determines when eluent rack magazine 31 is in an infeed position;
EM3—determines when eluent rack magazine 31 is empty;
EM4—determines when eluent rack magazine 70 is empty.

The sensors may be photodetectors or they may be magnetic, as appropriate and as desired.

The outputs of the detectors are sensed by a control system and the control system will react accordingly. There are certain safety interlocks built into the system to prevent any mechanical interference. The walking beam 100 must be in a position to present a cassette to channel A (sensor CA1) prior to movement of main carriage 74 forward, and the vacuum manifold 85 on elevator platform 84 must be down (sensor MCD). The walking beam will not move unless vacuum manifold 85 is down, that is, not in a position to engage the Luer nozzles 47. The eluent infeed magazines cannot move forward from their retracted positions unless the main carriage 74 is in its full forward position (sensor MCO). The main carriage 74 cannot move unless the manifold plate 91 is up and clear (sensor MMU). The manifold plate cannot move from its up or home position unless main carriage 74 is stopped on an index. The solvent pumps SP1-SP8 cannot operate unless the manifold plate is down (sensor MMD).

Figure 19:
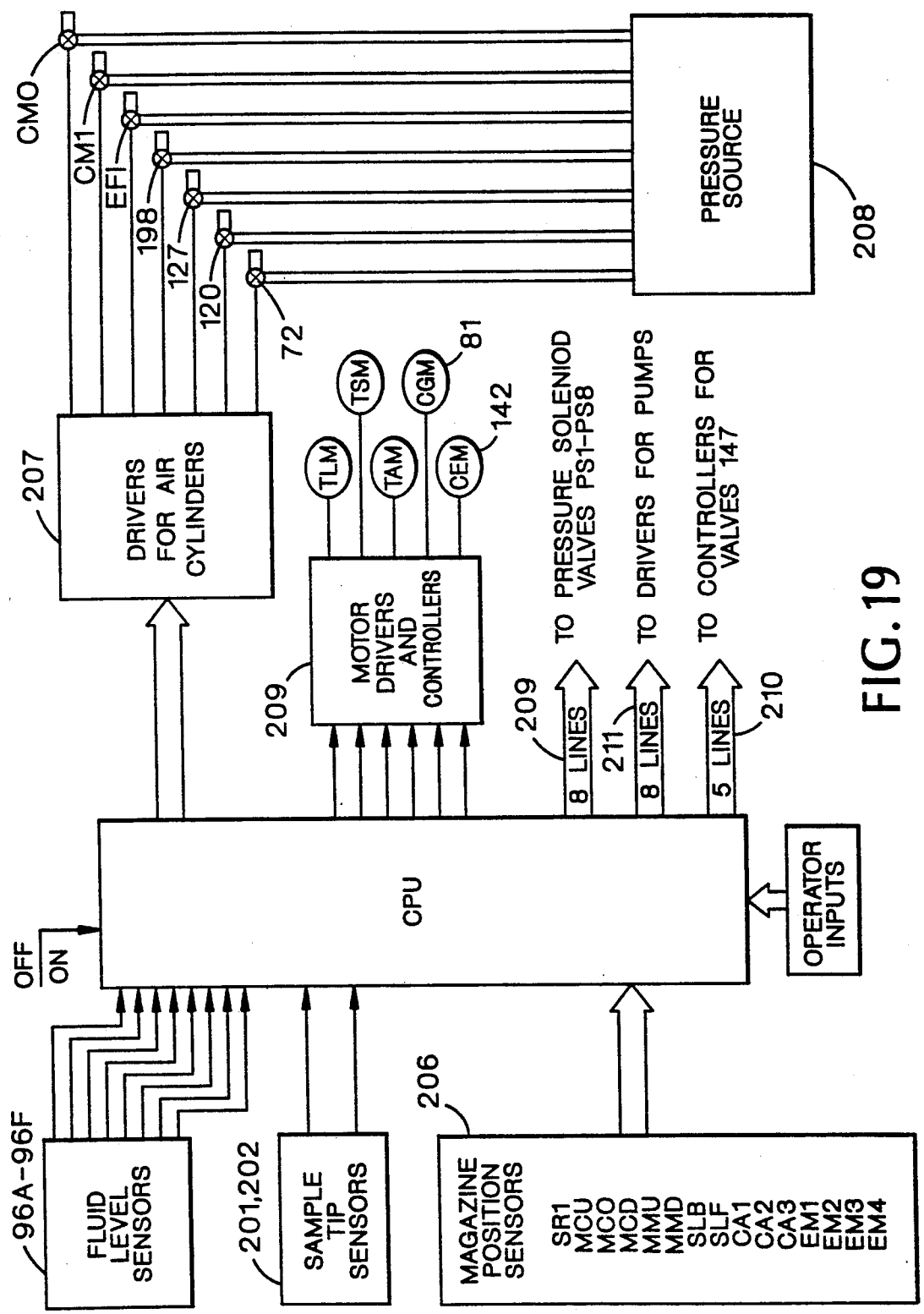
FIGS. 19 and 20 are schematic diagrams of the controls of the instrument.
Figure 20:
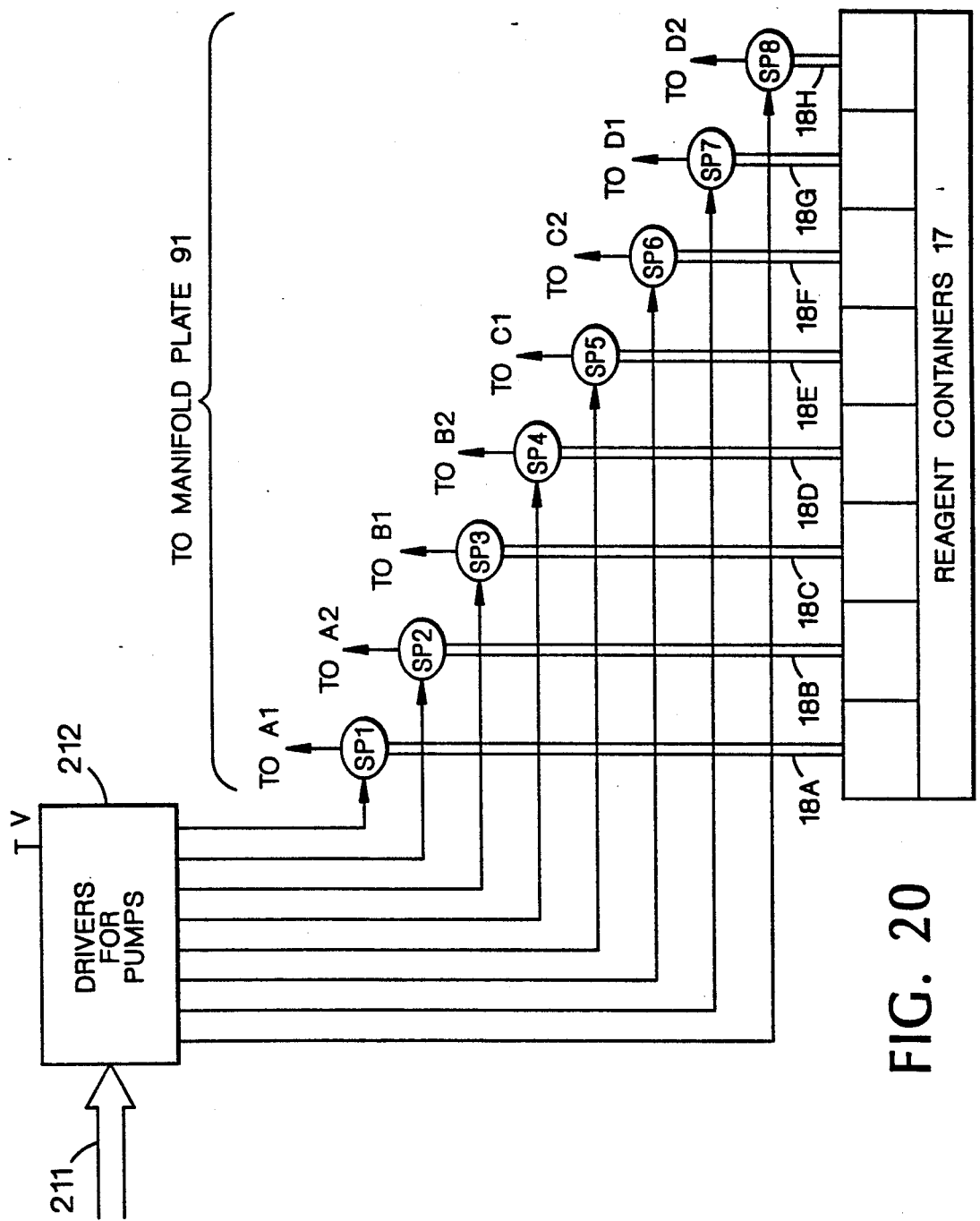

Reference is now made to FIG. 19 which schematically and in block form exemplifies the controls of the instrument. The controls include a microcomputer or a central processing unit (CPU) 205 which receives operator inputs from panel 13. The CPU receives inputs from the various position sensors indicated by the block 206, inputs from the sample tip sensors 201 and 202, and inputs from the fluid level sensors 96a-96f. In response to these inputs, and in accordance with the instrument programming, CPU 205 will provide signals to the drivers 207, for the stripper plate 22, cylinder 65 (not shown in FIG. 19), cylinder 72 for slide 71, walking beam cylinder 120, manifold plate cylinder 127, and channel C slide cylinder 198, previously described, as well as cylinder EFI for driving the eluent infeed magazine 31, the cassette infeed magazine cylinder CMI, and the cassette outfeed magazine cylinder CMO. When enabled, these cylinders will receive air pressure from a pressure source indicated at 208. CPU 205 further provides signals to motor drivers and controllers indicated at 209 for carriage drive motor (CGM) 81 and carriage elevator motor (CEM) 142, and also signals to the rotating drive motor for column 26 of aspirating arm 27 (TAM), the lift motor for column 26 (TLM) and the motor TSM for driving elbow 24. The CPU 205 will also provide eight outputs indicated at 209 to operate the pressure solenoid valves PS1-PS8 and provides five outputs indicated at 210 to operate the five valves 147 on vacuum manifold 85, and further supplies as indicated at 211, eight outputs to the drivers for pumps 212 for liquid through lines 18a–18h, respectively, from the reagent containers 17. The pumps SP1-SP8 dispense the various reagents utilized. Each is set to deliver a preset volume each time it is actuated. Higher volumes are obtained by repeating actuation of the pump.

It may thus be seen that the objects of the invention set forth, as well as those made apparent from the foregoing description, are efficiently attained. While a preferred embodiment of the invention has been set forth for purposes of disclosure, modifications to the disclosed embodiment of the invention, as well as other embodiments thereof, may occur to those skilled in the art. Accordingly, the appended claims are intended to cover all embodiments of the invention and modifications to the disclosed embodiments which do not depart from the spirit and scope of the invention.

Having thus described the invention, what is claimed is:

1. A system for effecting solid phase extraction from samples contacted by eluates into eluents, which system includes the use of cassettes which define a plurality of tubes each having an open top and having a lower opening, said tubes having an absorbent substrate therein between said upper and lower openings, said system comprising:
   (a) means providing storage for a plurality of said cassettes,
   (b) means for moving said cassettes past a plurality of stations to apply a preconditioning liquid to the absorbent substrates of said tubes, a sample to said tubes, and an eluate to said tubes,
   (c) said means for moving including means for selecting a first cassette from said storage means and positioning the selected cassette at a first of said stations,
   (d) means at said first of said stations for injecting said preconditioning liquid to said tubes to a predetermined height above said absorbent substrates and means for injecting a sample to be tested into said tubes at said first of said stations,
   (e) means at said first of said stations for drawing said preconditioning liquid into the absorbent substrate in said tubes and also the samples into said absorbent substrates after introduction of said samples,
   (f) said means for moving being effective to move said first cassette to another station while moving a second cassette to said first of said stations,
   (g) said means for moving being effective to move said first cassette to a further station while moving a third cassette to said first of said stations, and
   (h) means at said another station for injecting an eluate into the tubes of said first cassette, and means at said further station for removing an eluent from the lower opening of said tubes of a cassette into eluent receiving means.

2. The system of claim 1, including a second station where said another station is a third station, and means at said second station for introducing a washing liquid to tubes of cassettes thereat.

3. The system of claim 2 wherein said means for moving moves said cassettes in a linear direction, and includes second means for moving said means for moving to a second position in which liquid is deposited in the tubes of each cassette at said first and second stations at said second position.

4. The system of claim 3 further including a second further station which is a fourth station, said means for moving being effective to move a cassette from said further station to said second further station, means at said second further station for injecting second eluate into the tubes of a cassette thereat, and means at said second further station for removing an eluent from the tubes of a cassette thereat.

5. The system of claim 3 wherein means for injecting an eluate into the tubes of a cassette at said another station are at said second position of said means for moving.

6. The system of claim 5 wherein said means for drawing down said preconditioning liquid is also effective to draw down the sample into said absorbent substrates.

7. The system of claim 3 where said means for removing an eluent from said tubes at said further station includes either vacuum means applied to the lower openings of said tubes or means for applying pressure at the upper openings of said tubes.

8. The system of claim 3 whereby means are provided at said first station for monitoring the level of liquid in each tube.

9. The system of claim 3 wherein said absorbent substrate in said tubes is contained between top and bottom porous and inert frits.

10. The system of claim 3 where the means for drawing said preconditioning liquid into the absorbent substrate and also the samples comprises vacuum means applied to said lower openings.

11. The system of claim 10 further including means at said second station for blowing a drying gas through the tubes of a cassette thereat after introduction of the washing liquid.

12. The system of claim 11 wherein eluent is removed from the tubes of a cassette at said further station when said second means for moving means moves a cassette to said second position.

13. The system of claim 11 where said another station is a third station, and including means at said second station for introducing a washing liquid to the tubes of cassette thereat.

14. The system of claim 11 further including means at said first station for drawing the preconditioning liquid in the tubes of said first cassette down to a predetermined level whereby the absorbent substrates of the tubes of said first cassette are saturated with said preconditioning liquid.

15. The system of claim 14 further including means at said second station for blowing a drying gas through the tubes of a cassette thereat after introduction of the washing liquid.

16. A system for effecting solid phase extraction from samples contacted by eluates into eluents, which system includes the use of cassettes which define a plurality of tubes each having an open top and a lower opening, said tubes having an absorbent substrate therein between the open top and the lower openings, said system comprising:
 (a) means providing a storage for a plurality of cassettes,
 (b) first, second, third, and fourth stations for sequentially positioning said cassettes,
 (c) means for sequentially selecting a cassette from said storage means and sequentially moving each of the cassettes to said stations as a cassette is advanced from station to station,
 (d) means at said first station for injecting a sample into tubes of a cassette,
 (e) means at said first station for moving the sample through the tubes of a cassette into the absorbent substrate,
 (f) means at said second station for injecting an eluate into tubes of a cassette,
 (g) means at said third station for removing first eluent from said tubes into first individual eluent receiving means, and
 (h) means for injecting another eluate into said tubes after removal of the first eluent, and means at said fourth station for removing a second eluent from the tubes at said fourth station into second individual eluent receiving means.

17. A system for effecting solid phase extraction from samples contacted by eluates into eluents, which system includes the use of cassettes which define a plurality of tubes each having an open top and a lower opening, said tubes having an absorbent substrate therein between the open top and the lower openings, said system comprising:
 (a) means providing a storage for a plurality of said cassettes,
 (b) first, second, and third stations for sequentially positioning said cassettes,
 (c) means for sequentially selecting a cassette from said storage means and sequentially moving each of the cassettes to said stations as a cassette is advanced from station to station,
 (d) means at said first station for injecting a sample into tubes of a cassette,
 (e) means at said first station for moving the sample through the tubes of a cassette into the absorbent substrate,
 (f) means at said second station for injecting an eluate into tubes of a cassette, and
 (g) means at said third station for removing an eluent from said tubes into first individual eluent receiving means.

18. The system of claim 17 further including means at said first station where the liquid level in each tube is individually monitored.

* * * * *